(12) United States Patent
Schindler et al.

(10) Patent No.: US 8,834,772 B2
(45) Date of Patent: Sep. 16, 2014

(54) ANTIMICROBIAL METHACRYLATE CEMENTS

(75) Inventors: Katie M. Schindler, Fort Wayne, IN (US); Daniel B. Smith, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 100 days.

(21) Appl. No.: 13/313,764

(22) Filed: Dec. 7, 2011

(65) Prior Publication Data

US 2013/0150979 A1    Jun. 13, 2013

(51) Int. Cl.
*A61F 2/28* (2006.01)

(52) U.S. Cl.
USPC .................... 264/331.18; 424/423; 623/23.62

(58) Field of Classification Search
None
See application file for complete search history.

(56) References Cited

U.S. PATENT DOCUMENTS

| | | | |
|---|---|---|---|
| 4,239,113 A | 12/1980 | Gross et al. | |
| 4,373,217 A | 2/1983 | Draenert | |
| 4,869,906 A | 9/1989 | Dingeldein et al. | |
| 5,123,927 A | 6/1992 | Duncan et al. | |
| 5,217,493 A | 6/1993 | Raad et al. | |
| 5,258,420 A | 11/1993 | Posey-Dowty et al. | |
| 5,968,253 A | 10/1999 | Poser et al. | |
| 6,120,491 A | 9/2000 | Kohn et al. | |
| 6,155,812 A | 12/2000 | Smith et al. | |
| 6,160,033 A | 12/2000 | Nies | |
| 6,238,687 B1 | 5/2001 | Mao et al. | |
| 6,361,731 B1 | 3/2002 | Smith et al. | |
| 6,432,438 B1 | 8/2002 | Shukla | |
| 6,485,754 B1 | 11/2002 | Wenz et al. | |
| 7,427,296 B2 | 9/2008 | Evans | |
| 7,507,286 B2 | 3/2009 | Edidin et al. | |
| 7,594,578 B2 | 9/2009 | Smith et al. | |
| 7,637,729 B2 | 12/2009 | Hartman et al. | |
| 2004/0137065 A1 | 7/2004 | Vogt et al. | |
| 2005/0008620 A1* | 1/2005 | Shimp et al. | 424/93.7 |
| 2006/0171986 A1 | 8/2006 | Kuhn et al. | |
| 2006/0275339 A1 | 12/2006 | Schilke et al. | |
| 2006/0292199 A1 | 12/2006 | Kuhn et al. | |
| 2007/0122445 A1 | 5/2007 | Shalaby | |
| 2008/0058733 A1 | 3/2008 | Vogt et al. | |
| 2008/0058950 A1 | 3/2008 | Leonard et al. | |
| 2008/0063681 A1 | 3/2008 | Simon et al. | |
| 2008/0107707 A1 | 5/2008 | Lawson et al. | |
| 2008/0213336 A1 | 9/2008 | Kuhn et al. | |
| 2010/0110436 A1 | 5/2010 | Chandler et al. | |
| 2010/0152319 A1 | 6/2010 | Shalaby et al. | |
| 2010/0168271 A1 | 7/2010 | Beyar et al. | |
| 2010/0215716 A1 | 8/2010 | Troxel et al. | |
| 2010/0272649 A1 | 10/2010 | Nies et al. | |
| 2010/0292803 A1* | 11/2010 | Giori | 623/20.14 |
| 2011/0071072 A1 | 3/2011 | Calderone et al. | |
| 2012/0308633 A1* | 12/2012 | Shou-Cang et al. | 424/423 |
| 2013/0030058 A1* | 1/2013 | Vogt et al. | 514/772.6 |
| 2013/0072896 A1* | 3/2013 | Faccioli et al. | 604/500 |
| 2013/0150979 A1 | 6/2013 | Schindler et al. | |

FOREIGN PATENT DOCUMENTS

| | | |
|---|---|---|
| EP | 0328421 | 8/1989 |
| GB | 2093348 | 9/1982 |
| WO | WO 98/07458 | 2/1998 |

OTHER PUBLICATIONS

Barrack, R. "Rush Pin Technique for Temporary Antibiotic-Impregnated Cement Prosthesis for Infected Total Hip Arthroplasty" the Journal of Arthroplasty, vol. 17, No. 5 (2002), pp. 600-603.
Buchholz et al., Infektionsprophylaxe and operative Behandlung der schleichenden tiefen Infektion bei der totalen Endoprothese, Chirurg 43, 446-453 (1972).
Cambridge Polymer Group. User Manual: Cement Extrusion Tester. Version 1.0.1. Mar. 29, 2011.
Cui et al. "Antibiotic Impregnated Cement Spacers for the Treatment of Infection Associated with Total Hip or Knee Arthroplasty" J Bone Joint Surg Am. 2007; 89:871-82.
Durbhakula et al. "Spacer Endoprosthesis for the Treatment of Infected Total Hip Arthroplasty" J Arthroplasty. 2004; 19:760-7.
Goss et al. "Elution and Mechanical Properties of Antifungal Bone Cement" J Arthroplasty 2007; 22:902-8.
Hanssen et al. "Treatment of the Infected Total Knee Arthroplasty With Insertion of Another Prosthesis." Clin. Orthop 309:44. (1994).
Harsha et al. "Preparation and Evaluation of Gentamicin Biodegradable Polymeric Microspheres" Arch Pharm Sci & Res. vol. 1 No. 1:81-86. Jul. 2009.
Hospira Package Insert for Sterile Vancomycin Hydrochloride, USP Fliptop Vial for Intravenouse Use. wEN-2972v02, Revised Jan. 2012.
Jiranek et al. "Antibiotic-Loaded Bone Cement for Infection Prophylaxis in Total Joint Replacement" J Bone Joint Surg Am. 2006; 88:2487-2500.
Lentino, J. "Prosthetic Joint Infections: Bane of Orthopedists, Challenge for Infectious Disease Specialists" Clinical Infectious Diseases, vol. 36, No. 9 (pp. 1157-1161) May 2003.
Mader, J. et al. "Antibiotic Therapy for Musculoskeletal Infections" The Journal of Bone & Joint Surgery, vol. 83-A, No. 12 (pp. 1878-1890) Dec. 2001.

(Continued)

Primary Examiner — Mary F Theisen
(74) Attorney, Agent, or Firm — Hraness, Dickey (57) ABSTRACT

Bone cement compositions and methods of making two-part bone cements. The methods comprise transferring premixed powder and a liquid component into a receptacle, and mixing the powder component and the liquid component to form a cement composition. The premixed powder component comprises an acrylic polymer and a radical initiator. The bone cement is loaded with from about 5% to about 6% gentamicin by weight of the powder component, and from about 4% to about 5% vancomycin by weight of the powder component. The methods include filling a mold cavity with the bone cement composition to form a temporary spacer implant. The bone cement compositions provide a viscosity profile sufficient for the bone cement composition to flow within the mold cavity for an elapsed working time period of greater than about 6 minutes from the start of mixing at approximately 23° C.

20 Claims, 3 Drawing Sheets

(56) References Cited

OTHER PUBLICATIONS

Merck Manual, 16th Edition, Chapter 4 "Aminoglycosides." (1992).
Nelson et al. "A Comparison of Gentamicin Impregnated Polymethylmethacrylate Bead Implantation to Conventional Parental Antibiotic Therapy in Infected Total Knee Arthroplasty" Clin. Orthop. 295:96 (1993).
Price, J. et al. "Controlled release of antibiotics from coated orthopedic implants" Journal of Biomedical Materials Research, vol. 30 (pp. 281-286) 1996.
Principles of Critical Care, Chapter 40 "Principles of Antimicrobial Therapy and the Clinical Pharmacology of Antimicrobial Drugs." Second Edition. (pp. 671-717) 1998.
Provenzano et al. "Bone Cements: Review of Their Physiochemical and Biochemical Properties in Percutaneous Vertebroplasty." Ajnr Am J Neuroradiol 25:1286-1290, Aug. 2004.
Shah et al. "Evaluation of Drug Release Profile for a Combination of Antibiotics in a Calcium Sulfate Mixture." Ebi, Lp. 2007.
Shah et al. "Evaluation of Setting Times for Combinations of Bone Void Fillers mixed with Antibiotics" Ebi, Lp. 2007.
Tanzer et al. "Preoperative Assessment of Skin Colonization and Antibiotic Effectiveness in Total Knee Arthroplasty" Clin Orthop. 299:163 (1994).
Vancogenx: Winning Synergy.Tecres Medical. Revised 00/10.
Webb et al. "The Role of Polymethylmethacrylate Bone Cement in Modern Orthopaedic Surgery" Journal of Bone and Joint Surgery—vol. 89-B, Issue 7, 851-857 (2007).

\* cited by examiner

ANTIMICROBIAL METHACRYLATE CEMENTS

INTRODUCTION

The present technology relates to acrylate spacer cement loaded with a high dosage of antibiotics, and methods of manufacture.

The natural joints of the human body often undergo degenerative changes due to various etiologies. When these degenerative changes become so far advanced and irreversible, and unresponsive to non-operative management, it may ultimately become necessary to replace the natural joint with a prosthetic device. Due to any number of reasons, a small portion of patients (about 3%) that undergo such orthopedic surgical procedures suffer from infections at the surgical site and generally around the implanted joint prosthesis.

A common treatment for infections of many arthroplasty procedures is a two-stage revision. Typically, an infected joint prosthesis implant is removed and the site is thoroughly debrided and washed. An antibiotic solution is applied to the infected site and an antibiotic impregnated spacer implant, typically made primarily of acrylic bone cement, is temporarily placed in the patient until the infection is eliminated. The temporary spacer allows a patient to help maintain a natural range of motion, allows the patient to have partial weight bearing movement, serves as a local depot for antibiotic delivery while maintaining low serum concentrations of antibiotics, and maintains a soft tissue envelope for re-implantation. A new revision type joint prosthesis is then implanted during a subsequent orthopedic surgical procedure, after the infection is eradicated.

The antibiotic impregnated spacer implants may be custom made, and currently, surgeons are hand-mixing doses of antibiotics in bone cements using varying concentrations and combinations. This often results in little or no uniformity of predictable elution, mechanical, and handling properties of the spacer implants. In certain situations, the bone cement needs to be chilled in order to reduce its viscosity before the bone cement can be used to make a spacer implant. In other situations, the user may alter the bone cement composition, for example, the powder to liquid ratio, in order to obtain a suitable viscosity that will allow for the incorporation of additional antibiotics. Each such modification may alter the elution, mechanical, or handling properties of the cement in an unpredictable and uncharacterized manner.

Thus, although antibiotic impregnated spacers have many advantages, there remains a need to provide increased uniformity. For example, there remains a need for bone cement tailored to incorporate relatively large doses of antibiotics that has predictable elution, handling, and mechanical properties, and is suitable for the fabrication and fixation of temporary antibiotic impregnated joint spacers.

SUMMARY

The present technology provides a method of making a temporary spacer implant using a two-part bone cement. The method comprises transferring premixed powder and a liquid component into a mixing receptacle. The premixed powder component comprises an acrylic polymer and a radical initiator. The powder component also includes a gentamicin source providing gentamicin in an amount from about 5% to about 6% by weight of the powder component, and a vancomycin source providing vancomycin in an amount from about 4% to about 5% by weight of the powder component. The method includes mixing the powder polymer component and the liquid component to form a bone cement composition. A mold cavity is then filled with the bone cement composition to form a temporary spacer implant. The bone cement composition provides a viscosity profile sufficient for the bone cement composition to flow within the mold cavity for an elapsed working time period of greater than about 6 minutes from the start of mixing at approximately 23° C.

The present technology also provides a bone cement composition for forming a temporary spacer implant. The bone cement composition comprises a powder component including an acrylic polymer and a radical initiator. The composition includes a gentamicin source providing gentamicin in an amount from about 5% to about 6% by weight of the powder polymer component, and a vancomycin source providing vancomycin in an amount from about 4% to about 5% by weight of the powder polymer component. A liquid monomer component is also provided. A reaction of the powder polymer component and liquid monomer component provides a bone cement composition having a viscosity profile sufficient to yield a delivery time period of about six minutes from the onset of the reaction at a rate of about 7 cc/min at approximately 23° C. from an OPTIVAC® mixing cartridge, commercially available from Biomet, Inc., Warsaw, Ind., USA.

It should be noted that the figures set forth herein are intended to exemplify the general characteristics of materials, methods, and devices among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to antimicrobial methacrylate bone cements, and in particular, bone cements that can be used for preparing temporary spacer implants and the like. Bone cement that is used to form spacer implants is generally comprised of liquid and powder components, for example, a reactive liquid monomer component that polymerizes about a polymeric powder component. In this regard, bone cement is generally formed from a methyl methacrylate monomer and poly(methyl methacrylate) or methyl methacrylate-styrene homo- or copolymer. The powder component may contain polymer powder that in a known way is selected from homopolymers or copolymers of acrylic acid esters, methacrylic acid esters, styrene, vinyl derivatives or their mixtures. The reactive liquid may contain reactive organic monomers selected from methylmethacrylate, homolog esters of methacrylic acid or their mixtures.

The polymeric powder component of bone cement may comprise particles composed of spherical beads that may be obtained by a suspension polymerization process. The beads are generally sieved to comply with particular size specifications and desired mechanical properties. The polymeric powder component may also comprise particles that have been milled or crushed. The preparation of bone cement for an implant spacer generally involves mixing the polymer and monomer components in a suitable reaction vessel or mixing receptacle to form the bone cement composition. Generally, it is necessary that the components of bone cement be uniformly and thoroughly mixed so that a homogenous product is obtained. Increased homogeneity of the blend is particularly desirable in providing a cement mixture that is easy to work with, yet maintains satisfactory mechanical properties. In producing bone cement, it is typical to maintain the liquid and the powder components separate until just prior to use and to avoid exposure of the components to the atmosphere because of the potentially irritating and flammable nature of the bone cement components.

To keep the liquid and powder components separate, the two components may be stored in individual containers or packages. For example, the liquid component can be stored in a glass or polymeric ampoule and the powder component can be stored in a plastic pouch. An exemplary storage apparatus for the liquid component is described in U.S. Pat. No. 7,594,578, Smith et al., issued Sep. 29, 2009, incorporated by reference in its entirety.

The present technology relates to improved bone cements as well as methods for improving the antibiotic loaded temporary spacers made therefrom that may be used during two stage revisions. As used herein, the term "spacer" may be used to refer to an entire spacer, or a portion thereof. For example, a spacer made in accordance with the present technology, generally taking the shape of a permanent implant or prosthesis, may constitute the entire spacer, or it may be used with one or more pieces or components that together form a final spacer or spacer assembly. As such, the present technology encompasses a wide variety of therapeutic and cosmetic applications, in human or other animal subjects, and the specific materials and devices used must be biomedically acceptable. As used herein, such a "biomedically acceptable" component is one that is suitable for use with humans and/or animals without undue adverse side effects (such as toxicity, irritation, and allergic response) commensurate with a reasonable benefit risk/ratio.

The compositions of the present technology include one or more antibiotics that are effective to reduce, inhibit, or prevent the growth or transmission of foreign organisms in a patient. Preferably, the growth or transmission of a foreign organism is reduced, inhibited, or prevented in a statistically significant manner in at least one clinical outcome, or by any measure routinely used by persons of ordinary skill in the art as a diagnostic criterion in determining the same. The antibiotics may be used alone or in combination.

In various aspects, the antibiotics include aminoglycosides and glycopeptides, and in particular, gentamicin and vancomycin. As is known in the art, the bactericidal action of gentamicin is attributed to its ability to inhibit protein synthesis. The strength of this action is dependent on the concentration level of gentamicin. The reported range of minimum inhibitory concentrations (MIC) is from about 0.06 µg/ml to about 8 µg/ml. Gentamicin, and gentamicin sulfate in particular, is an important antibiotic used in the treatment of gram positive and gram negative aerobic bacterial infections. It has shown to not have much activity on anaerobes, fungi, or yeasts. Gram positive bacteria are typically less sensitive, with the exception of *Staphylococcus aureus* and *Staphylococcus epidermidis*, two strains that are important to device implant surgery. Gentamicin has been shown to be effective against aerobic gram negative and methicillin sensitive strains of *Staphylococcus* species but is less effective against methicillin resistant strains of *Staphylococcus* species. *Staphylococcus* species account for the majority of infected orthopedic implant related infections.

The gentamicin sulfate incorporated with the present technology may be recrystallized to a specific particle size range or distribution. In various aspects, the particle size range may be from about 50 µm to about 300 µm in diameter. The average particle size may be less than about 300 µm in diameter, less than about 275 µm in diameter, or less than about 250 µm in diameter. In various aspects, the average particle size may be greater than about 50 µm, greater than about 60 µm, or greater than about 75 µm. In certain aspects, the average particle size diameter is from about 60 µm to about 250 µm. For example, in certain aspects, about 98% or more of the particles used with the present technology may have a diameter larger than about 60 µm. Similarly, about 98% or more of the particles may have a diameter smaller than about 250 µm. The particles can be of a substantially homogenous particle size, or can be a mixture of at least two different particle sizes. Such a particle size range/distribution may allow for optimal elution characteristics for this type of acrylic spacer cement, as will be discussed. The gentamicin recrystallization process enhances the elution compared to the same gentamicin prior to recrystallization with smaller sized particles. In various aspects, the bone cement composition includes a gentamicin source providing gentamicin in an amount from about 2% to about 10% by weight of the powder component, from about 4% to about 8% by weight of the powder component, or from about 5% to about 6% by weight of the powder component. For example, when using a typical 40 g unit of powder polymer component, the gentamicin may be provided in an amount of about 2.4 g per unit of bone cement (for example, 40 g powder component and 20 ml liquid component).

As is known in the art, the bactericidal action of vancomycin is attributed to its ability to inhibit bacterial cell wall synthesis. The clinical pharmacology is dependent on the concentration level of vancomycin. The reported range of MIC is from about 0.12 to about 4 µg/ml. Vancomycin is proven to be effective against many aerobic and anaerobic gram positive bacteria strains, and has shown to be not effective against gram negative bacilli, mycobacteria, or fungi. Gram positive sensitive bacteria include *Staphylococcus aureus* and *Staphylococcus epidermidis* (including heterogenous methicillin resistant strains), two strains that are important to device implant surgery.

Some resistant *Staphylococcus* strains have been identified. In various aspects, the bone cement composition includes a vancomycin source providing vancomycin in an amount from about 2% to about 10% by weight of the powder component, from about 3% to about 7% by weight of the powder component, or from about 4% to about 5% by weight of the powder component. For example, when using a typical 40 g unit of powder polymer component, the vancomycin can be provided in an amount of about 2.0 g per unit of bone cement (for example, 40 g powder component and 20 ml liquid component). In various aspects, the particle size range may be from about 5 µm to about 350 µm in diameter. The average particle size of may be less than about 325 μm in diameter, less than about 300 μm in diameter, or less than about 250 μm in diameter. In various aspects, the average particle size may be greater than about 5 μm, or greater than about 10 μm. In certain aspects, the average particle size diameter is from about 10 μm to about 295 μm.

In general terms, polymeric cements become more viscous as more polymeric powder dissolves and absorbs liquid and as new polymer chains form and grow by reacting directly with the double bond of a monomer. While it is desirable to have a viscous bone cement to reduce and minimize leakage during mixing and filling mold cavities, viscous materials, such as hardening poly methylmethacrylate (PMMA), may harden very quickly once they reach and pass a threshold viscosity. Additionally, some bone fixing materials, such as PMMA emit heat while polymerizing (setting), and in certain instances need to be chilled prior to and during use in order to maintain a desired viscosity. In order to be most useful, the bone cement compositions should be balanced such that they are liquid enough during a working phase to be forced through a delivery device and to a mold, and otherwise flow under pressure to fill an entire mold cavity of a spacer implant mold.

The present technology provides for the use of an increased concentration and combination of gentamicin and vancomycin in a unique cement formulation that provides users with an acrylic spacer cement containing optimal and predictable elution, mechanical, and handling properties. At the same time, the present technology provides a suitable viscosity such that there is no need to pre-chill the bone cement composition, nor is there a need to use excess liquid monomer or aqueous solutions.

As discussed above, the viscosity of the compositions are sufficient to yield a delivery time of about 6 minutes from the onset of reaction at approximately 23° C., preferably using delivery devices among those known in the art. For example, the viscosity in some embodiments is such that the composition can be extruded from an OPTIVAC® mixing cartridge, which is a mixing receptacle/cartridge for bone cement commercially available from Biomet, Inc., Warsaw, Ind., USA. In various embodiments, the composition may be extruded at a rate of at least about 6 cc/min, at least about 7 cc/min, or at least about 8 cc/min, at a force of less than about 20 pounds at about 23° C.

As is known when working with bone cement, there are various phases of viscosity between the initial preparation of the composition and the hardened bone cement. Exemplary working data for mixing and applying Cobalt™ StageOne™ Acrylic Spacer Cement according to the present technology is provided in Tables 1 and 2, below. Table 1 provides delivery syringe mixing times at three typical ambient temperatures of surgical theaters; Table 2 provides open bowl mixing times at three typical ambient temperatures. As indicated for each temperature, the time for mixing is about 45 seconds. After the mixing, there may be a short wait phase, prior to the start of the application phase, for the viscosity to reach a desired consistency or homogeneity. Next, there may be a working or application phase, where the viscosity has reached a threshold value suitable for filling a cement spacer mold. The end of the application phase may be defined as the time after which the bone cement can no longer be delivered. Lastly, the hardening phase may be defined as the time after which the viscosity is essentially constant.

TABLE 1

| Ambient and Component Temperature | 17° C. | 20° C. | 23° C. |
|---|---|---|---|
| End of Mixing, Begin Wait Phase | 0'45" | 0'45" | 0'45" |
| Start of Application Phase (delivery into cement spacer mold) | 1'25" | 1'20" | 1'15" |
| End of Application Phase (delivery into cement spacer mold) | 10'15" | 8'00" | 6'00" |
| Hardening | 17'50" | 13'45" | 11'00" |

TABLE 2

| Ambient and Component Temperature | 17° C. | 20° C. | 23° C. |
|---|---|---|---|
| End of Mixing, Begin Wait Phase | 0'45" | 0'45" | 0'45" |
| Start of Application Phase | 4'45" | 4'07" | 3'30" |
| End of Application Phase | 10'00" | 8'00" | 6'30" |
| Hardening | 17'50" | 13'45" | 11'00" |

In various aspects, the polymeric powder component may be of a variety of different materials in a variety of different forms. For example, the polymeric powder component may comprise a poly(methyl methacrylate) or methyl methacrylate-styrene homo- or copolymer or methylmethacrylate-methylacrylate copolymer. The polymeric powder component may comprise various other forms or morphologies, such as spherical beads that can be obtained by any conventional suspension polymerization process. The beads may be sieved to comply with particular size specifications. The powder component may also comprise particles that have been milled or crushed, such as benzoyl peroxide from about 0.5% to about 5% by weight, and radiopacifiers, such as barium sulfate and zirconium dioxide, present in an amount from about 10% to about 20% by weight.

In the case of casting, the bone cement may be cast in an appropriate mold having a desired geometry according any method known in the art. Generally, casting of the cement may be performed at room temperature. It should be understood that typical surgical theaters may have operating temperatures ranging from about 15° C. to about 25° C. In many aspects, the temperature may be about 17° C.

The present technology also provides kits for an end user to produce bone cement on-demand in the field. Exemplary kits may comprise a bone cementing agent including gentamicin and vancomycin with the polmethylmethacrylate and/or methylmethacrylate. The bone cementing agent component may include a powder or a liquid comprising the cementing agent. The kit may include a bone cement liquid component, which may include a liquid monomer. As discussed, the bone cementing agent component may be packaged separately from any liquid component. Optionally, the kit includes instructions for use along with any tables that provide known useful formulations based on different amounts of components to achieve desired properties. Prior to filling a spacer mold, the cementing agent component and liquid component may be combined to form the bone cement for use by those skilled in the art.

The bone cements, compositions, methods, and kits described herein can be used with the fabrication and fixation of temporary joint spacers for the first stage of a two stage revision due to infection. In addition to being used to form a temporary spacer implant, the bone cement may be used to fix a spacer prosthesis or medical implant to a bone. Exemplary applications include arthroplasty procedures of the hip, knee, elbow and other anatomical locations. For example, the medical implant can be an orthopedic implant, for example, an acetabular cup, a knee implant, a shoulder implant, a femoral implant or femoral resurfacing system, a dental implant, a bone fixation device, scaffold, and the like. The medical implant can also be custom made or a generic shape for filling in a bone defect caused by surgical intervention or disease. As referenced herein, the term "implant" may refer to an entire implant as a whole, or a portion thereof; portions may be as large or as small as necessary to accommodate the specific need.

EXAMPLES

The compositions and methods of the present technology are exemplified in the following non-limiting Examples. Numerous bone cement compositions according to the present technology are prepared using a powder polymer component and a liquid monomer component as detailed below. The compositions are subsequently analyzed for antibiotic elution (results provided in Tables 5 and 6) and mean zones of inhibition for certain microorganisms (results provided in Tables 7 and 8).

For each example made in accordance with the present technology, a powder component is provided in a gas-permeable package including the following components as listed in Table 3:

TABLE 3

| | |
|---|---|
| Methylmethacrylate-methacrylate copolymer (with FD&C Blue No. 2 Aluminum Lake) | 33.42-33.57 g |
| Benzoyl peroxide, hydrous 75% | 0.40-0.70 g |
| Zirconium dioxide | 5.94 g |
| Gentamicin sulfate (equivalent to 2.4 g gentamicin) | 4.00 g |
| Vancomycin hydrochloride (equivalent to 2.0 g vancomycin) | 1.85 g |

For each example made in accordance with the present technology, a liquid component is provided in a flexible, pouch-like container. The flexible pouch consists of 20 ml of liquid (monomer) including the following components listed in Table 4.

TABLE 4

| | |
|---|---|
| Methylmethacrylate (stabilized with hydroquinone) | 18.424 g |
| N,N-dimethyl-p-toluidine | 0.376 g |

The powder component and gas-permeable package containing the powder component may be sterilized with gamma irradiation prior to mixing with a liquid component. The liquid monomer is sterile filtered and the exterior of the flexible pouch containing the liquid is sterilized with vaporous hydrogen peroxide.

The blue pigment (FD&C Blue No. 2 Aluminum Lake) added to the powder component is to produce a blue tint in the final cement, in order to distinguish between bone, soft tissue, and cement within the surgical field.

When the powder component is mixed with the liquid component, the N,N-dimethyl-p-toluidine activates the benzoyl peroxide catalyst in the powder, initiating polymerization of the monomer, which binds granules of polymer together. As the polymerization process proceeds, a viscous, flowable liquid is formed that can be injected into a spacer mold using a cement delivery system as known in the art. In various aspects, and as depicted in Tables 1 and 2, above, the flowable liquid can be delivered for a period of time between about 1 minute to about 10 minutes after mixing depending on the temperature and humidity of the surgical theater.

Figure 1:
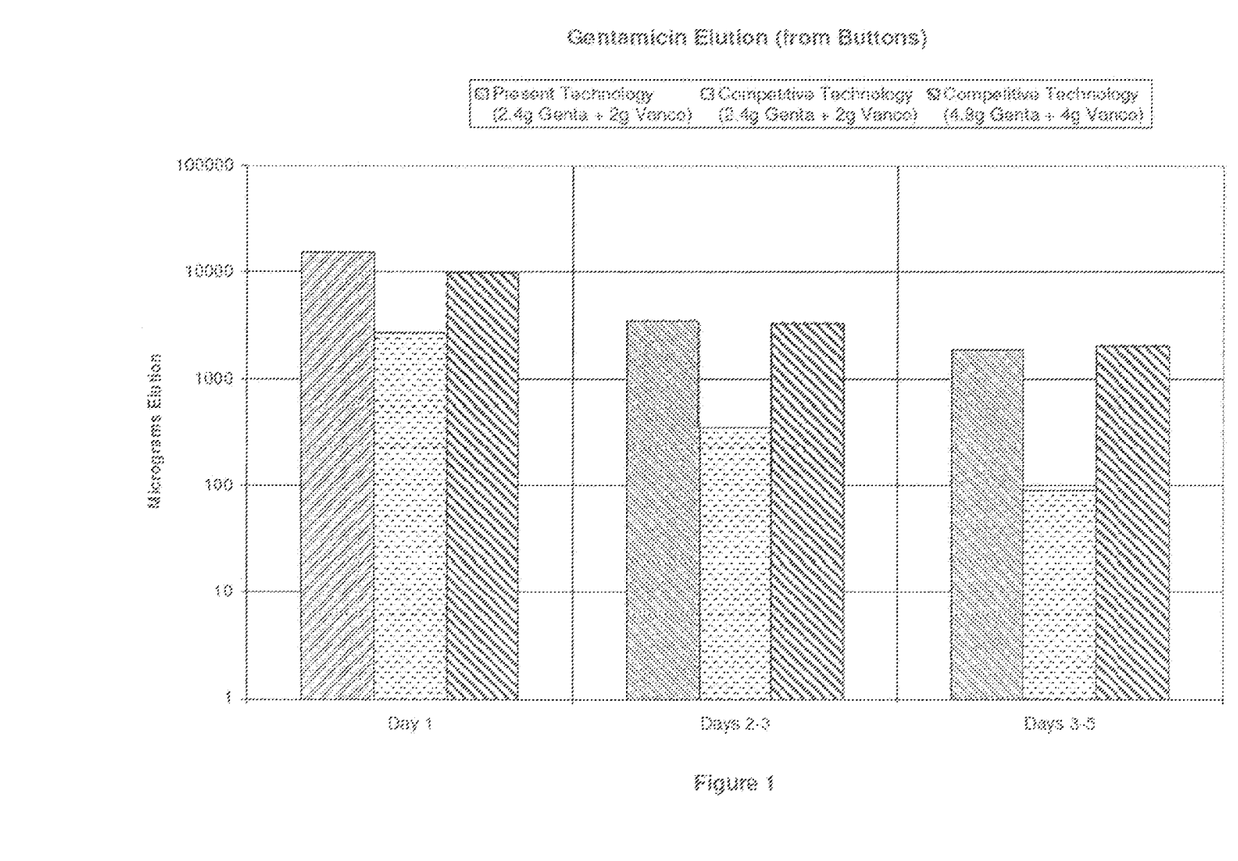
FIG. 1 is a bar graph representation of the elution of gentamicin from various bone cements for a period of between 1 and 5 days.
Figure 2:
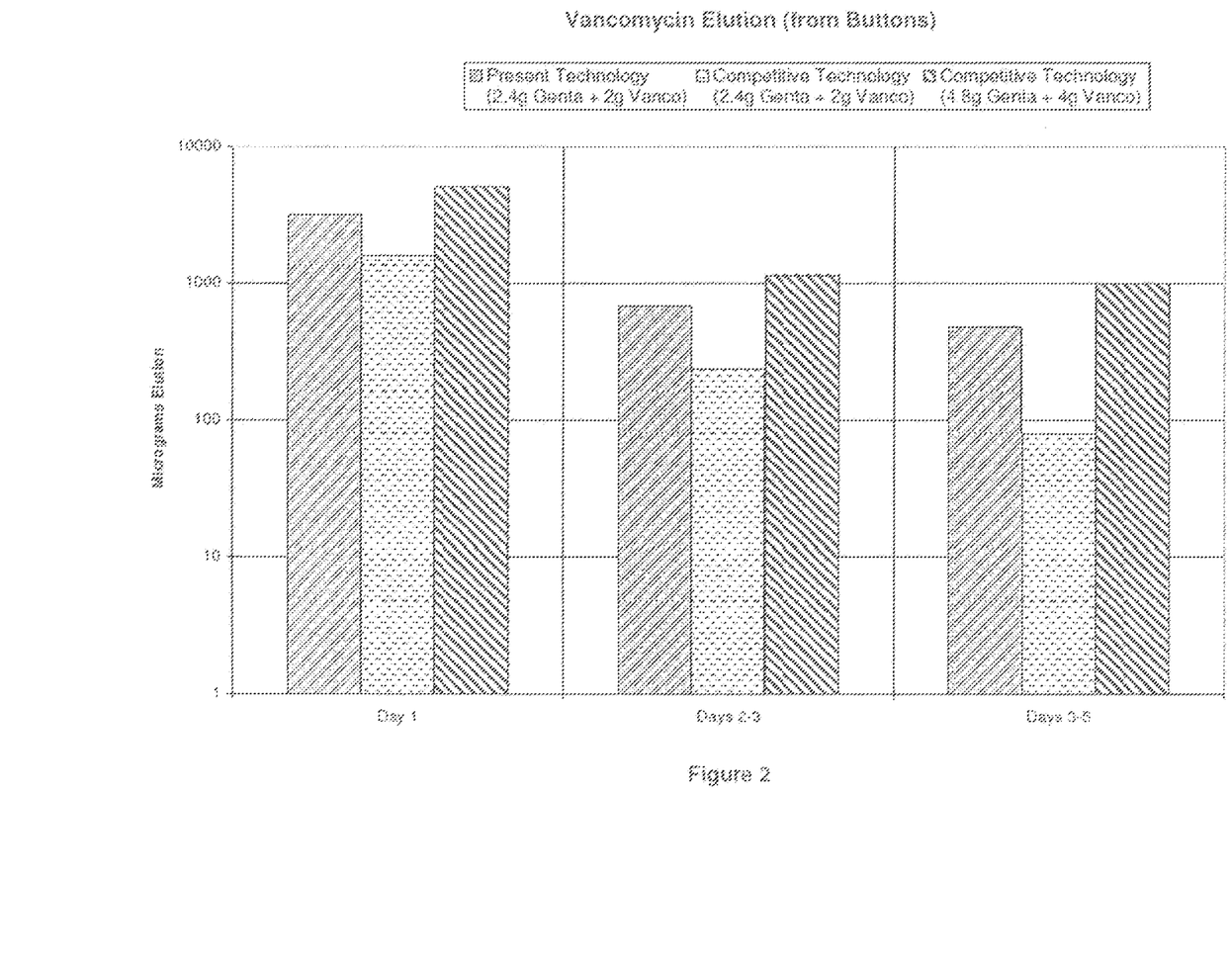
FIG. 2 is a bar graph representation of the elution of vancomycin from various bone cements for a period of between 1 and 5 days.

Tables 5 and 6, below, provide a comparison of the average elution of gentamicin and vancomycin for three different sets of bone cement compositions. The competitive technology sample sets (B) and (C) were created using Simplex P bone cement (commercially available from Stryker Corporation, Kalamazoo, Mich., USA) Sample set (B) contains the same amount of antibiotics as Sample set (A); Sample set (C) contains twice the amount of antibiotics as Sample (A). FIG. 1 is a bar graph representation of the elution of gentamicin from the various bone cements for the period of between 1 and 5 days. FIG. 2 is a bar graph representation of the elution of vancomycin from the various bone cements for the same period of between 1 and 5 days. The data presented is the amount eluted from cylindrical test coupons. For example, the coupons are prepared and the faces of the coupons are sanded with 80 grit sandpaper until the shine was just removed. Coupons are then placed in an aqueous solution for a period of about 1 to about 5 days. The data indicate that in order to obtain a similar elution with the competitive technology bone cements, one may have to use almost twice as much antibiotics—which is costly, may decrease the mechanical strength, and may affect the handling properties of the cement, and has the potential for increased waste of antibiotics.

In various aspects, the bone cement of the present technology may provide an elution of gentamicin in excess of about 875 μg/cm$^2$ within about 24 hours, and in excess of about 75 μg/cm$^2$ between about 48 and about 72 hours. In various aspects, the bone cement of the present technology may provide an elution of vancomycin in excess of about 175 μg/cm$^2$ within about 24 hours, and in excess of about 25 μg/cm$^2$ between about 48 and about 72 hours.

TABLE 5

| Gentamicin Elution | Day 1 (μg) | Days 2-3 (μg) | Days 3-5 (μg) |
|---|---|---|---|
| (A) Present Technology (2.4 g Gentamicin + 2 g Vancomycin) | 15434 | 3527 | 1897 |
| (B) Competitive Technology (2.4 g Gentamicin + 2 g Vancomycin) | 2774 | 354 | 89 |
| (C) Competitive Technology (4.8 g Gentamicin + 4 g Vancomycin) | 9969 | 3333 | 2073 |

TABLE 6

| Vancomycin Elution | Day 1 (μg) | Days 2-3 (μg) | Days 3-5 (μg) |
|---|---|---|---|
| (A) Present Technology (2.4 g Gentamicin + 2 g Vancomycin) | 3179 | 683 | 480 |
| (B) Competitive Technology (2.4 g Gentamicin + 2 g Vancomycin) | 1581 | 233 | 79 |

TABLE 6-continued

| Vancomycin Elution | Day 1 (µg) | Days 2-3 (µg) | Days 3-5 (µg) |
|---|---|---|---|
| (C) Competitive Technology (4.8 g Gentamicin + 4 g Vancomycin) | 5100 | 1141 | 993 |

Tables 7 and 8, below, provide a comparison of the mean zones of inhibition diameter (mm) for six common prosthetic joint infecting microorganisms using the eluates of antibiotic-bone cement compositions. The competitive technology samples were created using the Prostalac recommended formulation (DePuy's SmartSet Endurance MV bone cement hand mixed with 3.6 g of tobramycin sulfate and 1 g of vancomycin hydrochloride).

TABLE 7

Mean Zone of Inhibition Diameter (mm) for $10^0$ Eluate Dilution

| Microorganism | ATCC # | Present Technology (2.4 g Gentamicin + 2 g Vancomycin) | Competitive Technology (3.6 g Tobramycin + 1 g Vancomycin) | P-Value |
|---|---|---|---|---|
| Methicillin-resistant Staphylococcus aureus | 43300 | 21.1 ± 0.2 | 17.6 ± 0.3 | 0.000 |
| Methicillin-resistant Staphylococcus aureus | 700789 | 31.1 ± 1.1 | 13.8 ± 0.2 | 0.000 |
| Methicillin-resistant staphylococcus epidermidis | 51625 | 33.6 ± 1.0 | 30.4 ± 1.3 | 0.000 |
| Staphylococcus epidermidis | 12228 | 51.9 ± 1.2 | 50.9 ± 1.7 | 0.009 |
| Serratia marcescens | 29021 | 28.7 ± 0.9 | 20.8 ± 0.9 | 0.000 |
| Enterococcus faecalis | 49532 | 21.8 ± 0.6 | 16.3 ± 0.6 | 0.000 |

TABLE 8

Mean Zone of Inhibition Diameter (mm) for $10^{-1}$ Eluate Dilution

| Microorganism | ATCC # | Present Technology (2.4 g Gentamicin + 2 g Vancomycin) | Competitive Technology (3.6 g Tobramycin + 1 g Vancomycin) | P-Value |
|---|---|---|---|---|
| Methicillin-resistant Staphylococcus aureus | 43300 | 15.2 ± 0.5 | 9.7 ± 0.5 | 0.000 |
| Methicillin-resistant Staphylococcus aureus | 700789 | 21.3 ± 0.4 | 0 ± 0 | 0.000 |
| Methicillin-resistant staphylococcus epidermidis | 51625 | 21.8 ± 1.1 | 19.6 ± 2.6 | 0.027 |
| Staphylococcus epidermidis | 12228 | 42.1 ± 1.6 | 40.8 ± 1.7 | 0.003 |
| Serratia marcescens | 29021 | 19.9 ± 0.8 | 0 ± 0 | 0.000 |
| Enterococcus faecalis | 49532 | 11.3 ± 0.6 | 0 ± 0 | 0.000 |

TABLE 9

| Sample Set | Mean ISO Compressive Strength (MPa) | Mean ISO Compressive Modulus (MPa) | Mean ISO Bending Strength (MPa) | Mean ISO Bending Modulus (MPa) |
|---|---|---|---|---|
| (A) Present Technology (2.4 g Gentamicin + 2 g Vancomycin) | 99.1 | 2252 | 49.1 | 2666 |
| (B) Competitive Technology (3.6 g Tobramycin + 1 g Vancomycin) | 94.4 | 2198 | 38.1 | 1911 |

Table 9, below, provides a comparison of the mean ISO compressive strength, mean ISO compressive modulus, mean ISO bending strength, and mean ISO bending modulus for different sets of antibiotic bone cement compositions. The competitive technology samples (B) were created using the Prostalac recommended formulation (DePuy's SmartSet Endurance MV bone cement hand mixed with 3.6 g of tobramycin sulfate and 1 g of vancomycin hydrochloride). In various aspects, the bone cement provides an ISO bending strength in excess of about 49 MPa. In various aspects, the bone cement may also provide an ISO compressive strength in excess of about 99 MPa.

Table 10, below, provides a comparison of the delivery properties for different sets of antibiotic bone cement compositions. The competitive technology samples (B) are created using the Prostalac recommended formulation (DePuy's SmartSet Endurance MV bone cement hand mixed with 3.6 g of tobramycin and 1 g of vancomycin). The competitive technology samples (C) are created using the Hanssen's minimum recommended formulation (Stryker's Simplex P bone cement hand mixed with 2.4 g of gentamicin and 2 g of vancomycin). The competitive technology samples (D) are created using the Hanssen's typical recommended formulation (Stryker's Simplex P bone cement hand mixed with 4.8 g of gentamicin and 4 g of vancomycin). All samples are mixed in an OPTIVAC® mixing cartridge at approximately 23° C., and are then placed on a mechanical test machine between about 2 minutes 30 seconds and 3 minutes 15 seconds after the start of mixing. Actual start times are recorded and used for data analysis. The force required to extrude the cement from the OPTIVAC® at a rate of 7.2 cc/min was recorded.

TABLE 10

| Sample Set | Force required to extrude cement at 3:30 from start of mixing (lb$_f$) | Force required to extrude cement at 4:00 from start of mixing (lb$_f$) | Force required to extrude cement at 4:30 from start of mixing (lb$_f$) | Force required to extrude cement at 5:00 from start of mixing (lb$_f$) | Force required to extrude cement at 5:30 from start of mixing (lb$_f$) | Force required to extrude cement at 6:00 from start of mixing (lb$_f$) | Force required to extrude cement at 6:30 from start of mixing (lb$_f$) |
|---|---|---|---|---|---|---|---|
| (A) Present Technology (2.4 g Gentamicin + 2 g Vancomycin) | 5.14 | 6.04 | 6.91 | 8.14 | 9.88 | 12.58 | 17.37 |
| (B) Competitive Technology (3.6 g Tobramycin + 1 g Vancomycin) | 12.53 | 34.96 | 102.64 | 55.84 | 48.11 | 49.3 | 51.5 |
| (C) Competitive Technology (2.4 g Gentamicin + 2 g Vancomycin) | 5.51 | 6.73 | 8.42 | 10.4 | 12.74 | 15.59 | 19.45 |
| (D) Competitive Technology (4.8 g Gentamicin + 4 g Vancomycin) | 8.91 | 10.87 | 14.74 | 20.43 | 25.75 | 29.92 | 35.97 |

Figure 3:
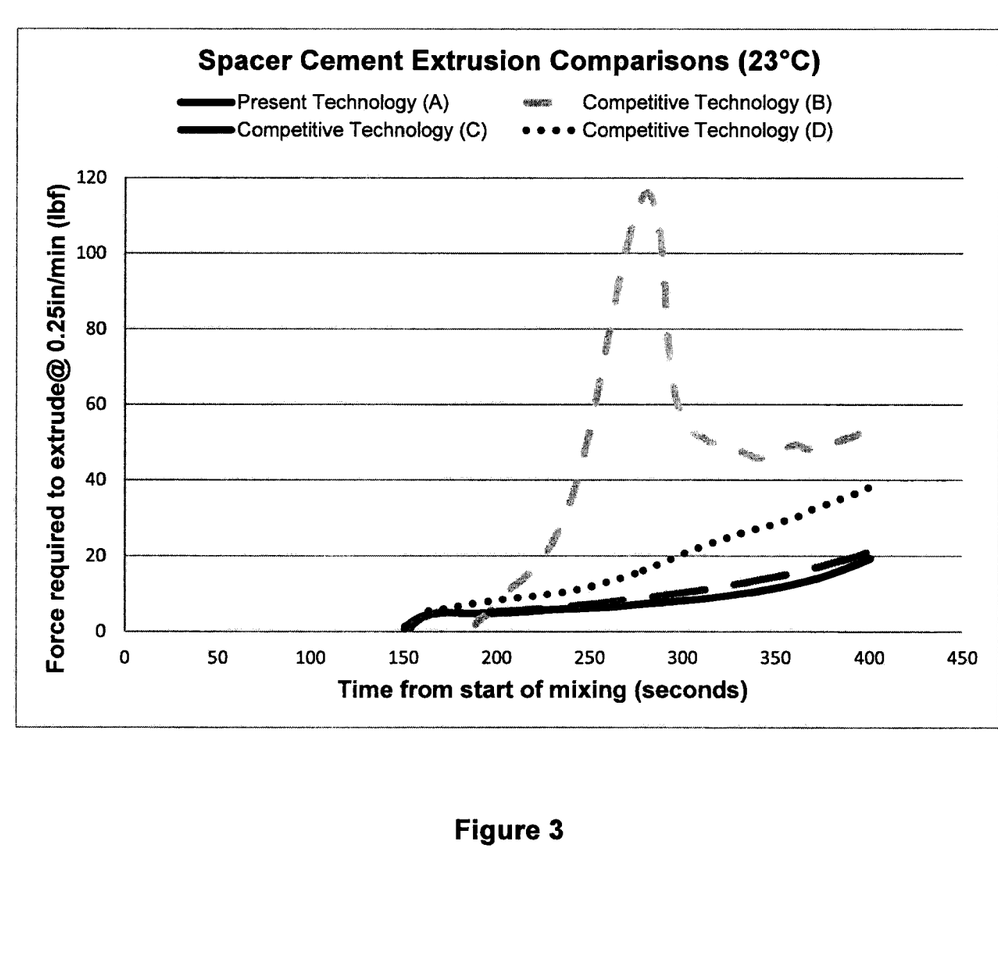
FIG. 3 is a scatter graph representation of the force required to extrude various bone cements from an OPTIVAC® mixing/collection/delivery system cartridge during optimal delivery conditions (up to about 6.5 minutes at about 23° C.).

FIG. 3 is a scatter graph representation of the force required to extrude the sample sets A, B, C, and D, using the data set forth in Table 10. As shown, the present technology provides the least amount of force required to extrude the cement at various times from the onset of mixing the components. In various aspects, the bone cement composition of the present technology maintains a viscosity profile suitable to extrude cement from a mixing cartridge at a rate of about 7 cc/min using a force of less than about 18 lb$_f$ during the working time period at about 23° C. It is believed that the force required for extrusion of the sample (B) competitive technology reached a high peak and then subsequently decreased before reaching a plateau region because of the morphology of the antibiotic therein causing and/or intensifying a blockage within the mixing cartridge.

The examples and other embodiments described herein are exemplary and not intended to be limiting in describing the full scope of the compositions and methods of the present technology. Equivalent changes, modifications, and variations of specific embodiments, materials, compositions, and methods may be made within the scope of the present technology, with substantially similar results.

Non-limiting Discussion of Terminology:

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "preferably," "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. A method of making a temporary spacer implant using a two-part bone cement, the method comprising:
    transferring premixed powder and a liquid component into a mixing receptacle, the premixed powder component comprising:
        an acrylic polymer;
        a radical initiator;
        a gentamicin source providing gentamicin in an amount from about 5% to about 6% by weight of the powder component, wherein the gentamicin source comprises gentamicin sulfate that is recrystallized having a mean particle size diameter from about 60 μm to about 250 μm; and
        a vancomycin source providing vancomycin in an amount from about 4% to about 5% by weight of the powder component;
    mixing the powder polymer component and the liquid component to form a bone cement composition; and
    filling a mold cavity with the bone cement composition to form a temporary spacer implant, wherein the bone cement composition provides a viscosity profile sufficient for the bone cement composition to flow within the mold cavity for an elapsed working time period of greater than about 6 minutes from the start of mixing at approximately 23° C.

2. The method of claim 1, wherein the bone cement composition maintains a viscosity profile suitable to extrude cement from an OPTIVAC® mixing cartridge at a rate of about 7 cc/min using a force of less than about 18 lb$_f$ during a working time period at about 23° C.

3. The method of claim 1, wherein the powder polymer component is sterilized using gamma irradiation prior to mixing with the liquid component.

4. The method of claim 1, wherein the vancomycin source comprises vancomycin hydrochloride.

5. The method of claim 4, wherein the vancomycin hydrochloride has a mean particle size diameter from about 10 μm to about 295 μm.

6. The method of claim 1, wherein the liquid component comprises methylmethacrylate and a radical activator.

7. The method of claim 1, wherein the acrylic polymer comprises methylmethacrylate-methylacrylate copolymer.

8. The method of claim 1, wherein the bone cement has an ISO bending strength in excess of about 49 MPa after hardening.

9. The method of claim 1, wherein the bone cement has an ISO compressive strength in excess of about 99 MPa after hardening.

10. A bone cement for forming a temporary spacer implant, the bone cement comprising:
    a powder component comprising:
        (a) an acrylic polymer;
        (b) a radical initiator;
        (c) a gentamicin source providing gentamicin in an amount from about 5% to about 6% by weight of the powder polymer component, wherein the gentamicin source comprises gentamicin sulfate that is recrystallized having a mean particle size diameter from about 60 μm to about 250 μm; and
        (d) a vancomycin source providing vancomycin in an amount from about 4% to about 5% by weight of the powder polymer component;
    a liquid monomer component,
    wherein a reaction of the powder polymer component and liquid monomer component provides a bone cement composition having a viscosity profile sufficient to yield a delivery time period of about 6 minutes from the onset of the reaction at approximately 23° C.

11. The bone cement of claim 10, comprising a viscosity profile suitable to extrude cement from an OPTIVAC® mixing cartridge at a rate of about 7 cc/min using a force of less than about 18 lb$_f$ during a working time period at about 23° C.

12. The bone cement of claim 10, wherein the acrylic polymer comprises methylmethacrylate-methylacrylate copolymer and a radical initiator.

13. The bone cement of claim 10, providing an elution of gentamicin in excess of about 880 ug/cm² within about 24 hours.

14. The bone cement of claim 10, providing an elution of gentamicin in excess of about 78 ug/cm² between about 48 and 72 hours.

15. The bone cement of claim 10, wherein the vancomycin source comprises vancomycin hydrochloride.

16. The bone cement of claim 15, wherein the vancomycin hydrochloride has a mean particle size diameter from about 10 μm to about 295 μm.

17. The bone cement of claim 10, providing an elution of vancomycin in excess of about 174 ug/cm² within about 24 hours.

18. The bone cement of claim 10, providing an elution of vancomycin in excess of about 25 ug/cm² between about 48 and 72 hours.

19. The bone cement of claim 10, comprising an ISO bending strength in excess of about 49 MPa after hardening.

20. The bone cement of claim 10, comprising an ISO compressive strength in excess of about 99 MPa after hardening.

* * * * *